United States Patent [19]

Averette

[11] Patent Number: 4,896,545

[45] Date of Patent: Jan. 30, 1990

[54] AUTOMATIC FLUID INJECTOR

[75] Inventor: Julius P. Averette, Baker, La.

[73] Assignee: Dynatech Precision Sampling Corporation, Baton Rouge, La.

[21] Appl. No.: 184,797

[22] Filed: Apr. 22, 1988

[51] Int. Cl.$^4$ ............................................. G01N 35/06
[52] U.S. Cl. .................. 73/863.01; 73/864.21.864.22;
73/864.82; 73/864.84; 73/864.86; 73/864.87
[58] Field of Search ............ 73/863.01, 863.02, 863.03,
73/863.71, 863.73, 863.81, 863.82, 863.83,
864.84, 863.85, 863.86, 864.15, 864.21, 864.22,
864.24, 864.25, 864.81, 864.82, 864.83, 864.84,
864.85.864.86, 864.87

[56] References Cited

U.S. PATENT DOCUMENTS

| | | | |
|---|---|---|---|
| 3,754,443 | 8/1973 | Harris, Sr. et al. | 73/863.81 |
| 3,824,859 | 7/1974 | Harris, Sr. et al. | 73/864.87 |
| 3,885,438 | 5/1975 | Harris, Sr. et al. | 73/863.81 |
| 3,940,995 | 3/1976 | Harris, Sr. et al. | 73/863.81 |
| 4,044,616 | 8/1977 | Harris, Sr. et al. | 73/863.81 |
| 4,283,128 | 8/1981 | Mayer et al. | 250/301 X |
| 4,372,150 | 2/1983 | Stephens et al. | 73/61.1 X |
| 4,646,562 | 3/1987 | Cronan | 73/64.4 |
| 4,736,639 | 4/1988 | Averette | 73/863.81 X |
| 4,775,481 | 10/1988 | Allington | 210/101 X |
| 4,781,824 | 11/1988 | Allington | 210/198.2 X |

Primary Examiner—Tom Noland
Attorney, Agent, or Firm—Llewellyn A. Proctor

[57] ABSTRACT

An automated fluid injector which includes, in combination, (A) a syringe, (B) an injector feed assembly for introducing a fluid specimen into the syringe, (C) a magazine for transporting fluid specimens for pick up by the injector feed assembly, and (D) an automatic drop counter. The automatic drop counter counts drops of a fluid specimen overflowed from the barrel, and is responsive to a preselected drop count to cut off the flow of fluid specimen transported from a vial by the probe sub-assembly, and trap a calibrated amount of the fluid specimen for injection. The automatic drop counter can also be used as a safety mechanism to shut down the operation of the instrument when no flow occurs over a preselected interval of time. By virtue of this combination, a wide range of highly volatile and highly viscous fluid specimens can be handled.

10 Claims, 7 Drawing Sheets

AUTOMATIC FLUID INJECTOR

FIELD OF THE INVENTION

This invention relates to improvements in automatic fluid injectors, or automated syringes. In particular, it relates to improvements in loading automatic fluid injectors, or syringes, for improving their precision and accuracy in handling highly volatile or highly viscous fluid specimens.

BACKGROUND AND PROBLEMS

Automated fluid injection devices, particularly automated needle syringes, have gained wide acceptance by industry and by the scientific and medical communities. This is because these devices are generally capable of dispensing very small, accurately measured quantities of fluid specimens on the order of a few microliters, generally a fractional part of a microliter up to about 50 microliters with high accuracy and precision. Moreover, the advantages offered by modern data gathering techniques, and consequent reduction in operating manpower without loss in accuracy make these devices particularly useful in modern industrial establishments.

Typically, in the operation of an automated fluid injection device, septum covered vials are charged with a fluid specimen and transported in seratim via a magazine to a station adjacent a probe assembly, a needle of the probe assembly is projected through the septum of a vial and employed as a conduit to convey a portion of the fluid specimen to the barrel of the syringe. The circuit through which the specimen is conducted, and barrel and needle of the syringe are cleaned, purged and a quantity of the fluid specimen is measured out and injected via the needle end of the syringe into the inlet of an analytical instrument, e.g., a G.C. or mass spectrometer.

Time, pressure and the relationship between time and pressure are critical parameters in designing instruments of this type. Pressure is the driving force for movement of a fluid specimen from a vial to the barrel of the syringe and the rate of movement of the fluid specimen is directly related to the viscosity of the fluid specimen. The higher the viscosity of the fluid specimen at a given pressure the slower its rate of movement. Conversely, the lower the viscosity of the fluid specimen at a given pressure the greater the rate of movement of the fluid specimen. Consequently, whereas automatic fluid injectors have served admirably well, they nonetheless prove unreliable, and even fail in handling highly volatile or highly viscous fluid specimens. For example, the accuracy and precision of these instruments in handling fluid specimens of high volatility, e.g., hexane which measures about 0.3 centipoises, and fluid specimens of low volatility, e.g., propylene glycol which measures about 50.0 centipoises, at best leaves much to be desired in terms of accuracy and precision, and at worse fails miserably. In handling the more volatile specimens, the specimens on delivery to the barrel and needle portion of the fluid injection device thus flow too freely and thus drain too rapidly from the dispensing end of the needle. Thus, the barrel and needle are not completely filled. In handling the more viscous specimens, the fluid flows so slowly from the pick up station to the barrel and needle portion of the fluid injection device that the barrel and needle are not adequately filled. For these reasons, it becomes virtually impossible to handle at one time a set of vials loaded with fluid specimens of a wide range of viscosities, and virtually impossible to adjust the cycle length of the cleaning, purging and filling operation over the range of viscosities necessary for many fluid sampling operations. Highly viscous fluids are per se difficult to handle in conventional fluid injection devices, and many viscous fluids simply cannot be handled by conventional fluid injection devices. There is thus a need for improved automatic fluid injectors capable of loading and injecting, with accuracy and precision, highly volatile fluid specimens and highly viscous fluid specimens, particularly the latter, and more particularly fluid specimens of a set having a range of differing viscosities.

OBJECTS

It is, accordingly, a primary object of the present invention to satisfy this and other needs.

A specific object is to provide apparatus capable of continuously withdrawing, preferably cyclically seriatly withdrawing liquid specimens, especially highly volatile and highly viscous liquid specimens, from prefilled septum covered vials, and loading these specimens in seriatim with precision and accuracy into a calibrated bore or barrel, preferably the bore of the barrel and needle of the automatic fluid injector, or syringe, by overflowing the calibrated bore, or barrel and needle, counting the drops of liquid overflowed, and then cutting off the flow when the bore or barrel is filled, or purged of previous containinant, cleaned and filled.

A further, and more specific objective is to provide apparatus of simple and relatively inexpensive construction, particularly apparatus which can be readily serviced and operated, which readily lends itself to rapid mass production techniques.

SUMMARY OF THE INVENTION

These objects and others are achieved in accordance with the present invention which embodies improvements in fluid injection devices of type wherein a fluid specimen is picked up from a supply source, at least a portion thereof is charged to calibrated chamber or barrel, the chamber or barrel is filled, or purged of previous containinant, and cleaned and then filled with a portion of the fluid specimen which overflows the chamber or barrel, the drops of liquid specimen overflowing the barrel are counted via counting means up to a preselected number, the filled chamber or barrel is then closed via closure means, and the specimen then injected into a medium with accuracy and precision.

The present invention preferably embodies improvements in fluid injector devices, particularly automatic fluid injector systems which include the combination of (A) a syringe, or syringe assembly inclusive of a barrel into which a fluid specimen can be loaded, overflowed via an outlet from said barrel as liquid drops, and a calibrated amount of the fluid specimen trapped in said barrel, and means for the displacement of trapped specimen from the barrel into a media, e.g., the septum inlet of an analytical instrument, (B) an injector feed assembly comprised of a probe sub-assembly inclusive of hollow needles, especially a pair of concentrically mounted hollow needles which provide a conduit for the pick up of said fluid specimen from a vial, and transport thereof into the barrel of said syringe, (C) a magazine for transporting one or more fluid specimen-containing septum sealed vials for pick up of fluid specimen by the probe sub-assembly of said injector feed probe sub-assembly for delivery to the barrel of said syringe for subsequent injection into said media, and (D) automatic drop counter means for counting liquid drops overflowed from the barrel via said barrel outlet and responding to a preselected drop count to interrupt the flow of fluid specimen transported from a vial by the probe sub-assembly of said injector feed assembly and trap a calibrated amount of the fluid specimen within the barrel of said syringe, or syringe assembly, for subsequent injection. The drop counter can also be set to detect an interruption in flow persisting over a preselected period, as may occur on breakage of a transfer line, and hence is also useful as a safety device.

In prior art instruments of this type the flow of fluid specimen from a vial through the probe sub-assembly to the barrel of the syringe is conducted by pressurizing the fluid contents of the vial over a preselected discrete period of time. Unfortunately, the entire fluid contents of a vial can be completely discharged, and the syringe barrel partially or completely emptied if the time is too long. On the other hand, the contents of a very viscous fluid specimen may not completely fill the barrel, or possibly never reach the barrel if the period of time is too short. Failure to completely fill the barrel will result in delivery to the septum inlet of the instrument less than the calibrated amount of the fluid specimen, this interfering with the accuracy of the measurement, and loss of precision due to an accumulation of inaccurate measurements. Quite obviously, the handling of a variety of fluid specimens having a range of different viscosities can introduce many problems. Thus, on the one hand, to accommodate a highly volatile solvent a very short time period must be set, a time period which may not allow adequate delivery of a more viscous fluid from a vial via the probe sub-assembly to the barrel of the syringe. Conversely, if the time period is sufficiently long to adequately and precisely discharge from a vial a highly viscous fluid specimen, highly volatile fluid specimens may be emptied from the barrel of the syringe as well as from the vial in which it is contained. Even where relatively volatile fluid specimens are analyzed which offer a fairly narrow range of viscosities, the period required for the withdrawal of each of the specimens from a vial cannot be idealized, and consequently considerably more of the fluid specimen must be supplied to a given vial than may be desired to achieve proper overall operation. This, of course, is burdensome; particularly when the availability of the specimen is limited. The difficulty of optimizing the withdrawal period is even more burdensome where the fluid specimens to be analyzed are highly viscous; and becomes virtually impossible, if not impossible, when both highly volatile and highly viscous fluid specimens are to be analyzed.

The invention, and its principle of operation, will be more fully understood by reference to the following detailed description of a specific and preferred embodiment, and to the attached drawings to which reference is made in the description. Similar numbers are used in the description to represent similar parts or components, and subscripts are used with numbers where parts or components are duplicated. Where reference is made in the written text to a component designated by the use of subscripts in the drawing, without reference to the subscripts, the designation is intended in a generic sense.

In the drawings:

FIG. 1 depicts a side elevation view of an automatic fluid injector as known and described in U.S. Pat. No. 4,736,639, issued Apr. 12, 1988, which includes a platform on which is mounted a carriage, reciprocably movable thereupon, which carries (A) a syringe, or syringe assembly inclusive of a barrel on the rearward end of which is mounted a valve, and forward end on which is mounted a needle, (B) an injector feed unit, inclusive of its probe assembly which is shown in raised position, and (C) a carrousel type magazine, or feed tray, which carries fluid specimen-containing vials for pick up of specimen therefrom by the probe assembly for delivery to the syringe, or syringe assembly.

FIG. 2 is Section 2—2 of FIG. 1, this view depicting in plan principally the syringe, or syringe assembly, mounted upon its carriage which is reciprocably movable upon the platform of said automatic fluid injector.

FIG. 3 depicts a side elevation view of a portion of the automatic fluid injector and automatic drop counter means, wherein in said automatic fluid injector the syringe, or syringe assembly is depicted in partial section, and the probe assembly of the injector feed unit is shown in lowered position as positioned in withdrawing a fluid specimen from a vial delivered by said magazine, or feed tray, for loading a fluid specimen therefrom into the barrel of the syringe, and the valve and needle portion of the syringe is retracted to its rearward position relative to the carriage within which it is transported for filling the barrel of the syringe with a portion of the fluid specimen, the fluid overflowing the syringe barrel and being delivered (via a fluid diversion valve, Section 3A—3A of FIG. 3 as depicted in FIG. 3A) as droplets to the automatic drop counter.

DETAILED DESCRIPTION OF THE INVENTION

Figure 1:
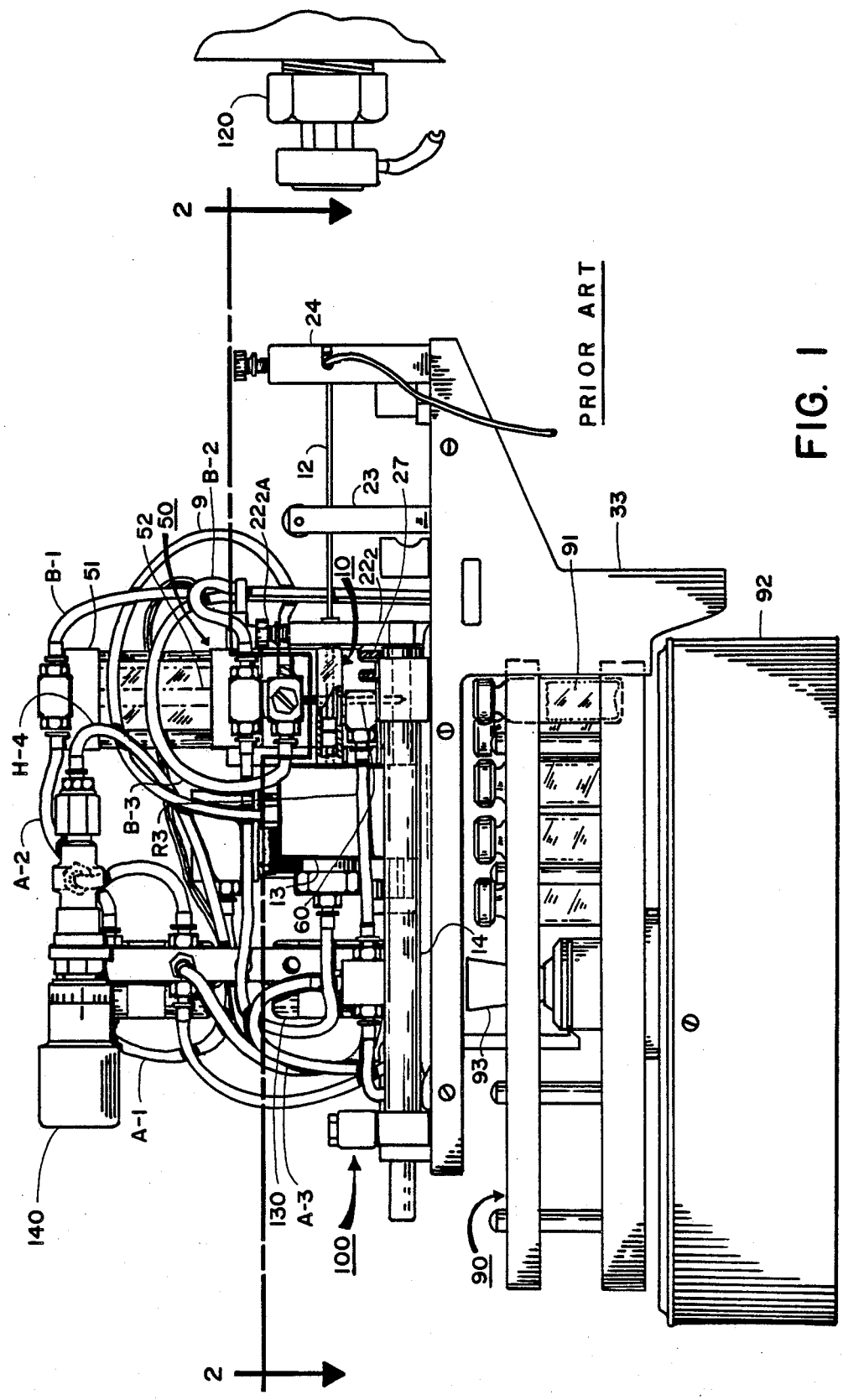

Reference is made, first generally, to the figures, which shows a preferred automatic fluid injector and automatic drop counter. The principle sub-assemblies of the automatic fluid injector 100 include (A) a syringe, or syringe assembly 10, (B) an injector feed assembly 50, inclusive of a reciprocable probe assembly 60 (or pair of concentric hollow probes), the details of which are best given by reference to FIG. 6, which is used to pick up a fluid specimen for delivery of same to the syringe, or syringe assembly 10, (C) a magazine or carrousel type feed tray 90 for transporting one and preferably a plurality of vials of fluid specimens to a location for pick up by said probe assembly 60 of said injector feed assembly 50, and (D) an automatic drop counter 150. Portions of fluid specimens are picked up in serial fashion from the individual vials and injected in seriatim in accurately measured quantities into e.g., an inlet 120 of an analytical instrument, via the direct action of the syringe, or syringe sub-assembly 10. The sub-assemblies (A), (B), and (C) may be contained in whole or in part within a casing, housing or framed structure and are responsive to automatic control means such as described in U.S. Pat. No. 3,754,443. The principle features and overall function of these several sub-assemblies and their relation one to another are generally as follows:

(A) The syringe, or syringe sub-assembly 10, (FIG. 9), is constituted of a syringe per se which includes a barrel 11 on one end of which is mounted a cannula, or needle 12, and on the opposite end of which is mounted a valve 13. A fluid specimen introduced into the barrel 11 via valve 13 flows through the bore of the barrel and the opening through the needle 12. On the rearward terminal end of the needle 12 is affixed a tubular seal $12_1$ which fits snugly and concentrically within the bore of the barrel 11, within which the needle 12 is reciprocably movable via movement of the barrel 11 relative thereto over a limited distance defined by a zero fill position, and a preselected pre-set maximum fill position. The valve 13 is mounted on the opposite end of the barrel 11. The valve 13 provides an open position and closed position. In its open position the valve 13 can admit a fluid specimen delivered from a vial via action of the probe assembly 60 of the injector feed assembly 50 into the bore of the barrel 11. In its closed position the flow of the fluid specimen into the barrel is interrupted, and fluid specimen is retained within the bore of the barrel 11 for injection via the dispensing end $12_2$ (FIG. 7) of the needle 12. In its filling and injection function, the bore of barrel 11 of the syringe is filled via specimen fill line 9 through which a fluid specimen is conveyed via the open valve 13, then the valve 13 is closed, the dispensing end $12_2$ of the needle 12 is thrust into a medium, e.g., septum inlet 120, and the valve 13-barrel 11 sub-assembly then moved relative to needle 12 to displace fluid specimen from the barrel 11 through the distal, or dispensing end $12_2$ of the needle 12. The mechanism by which this function is accomplished will be subsequently described.

Figure 2:
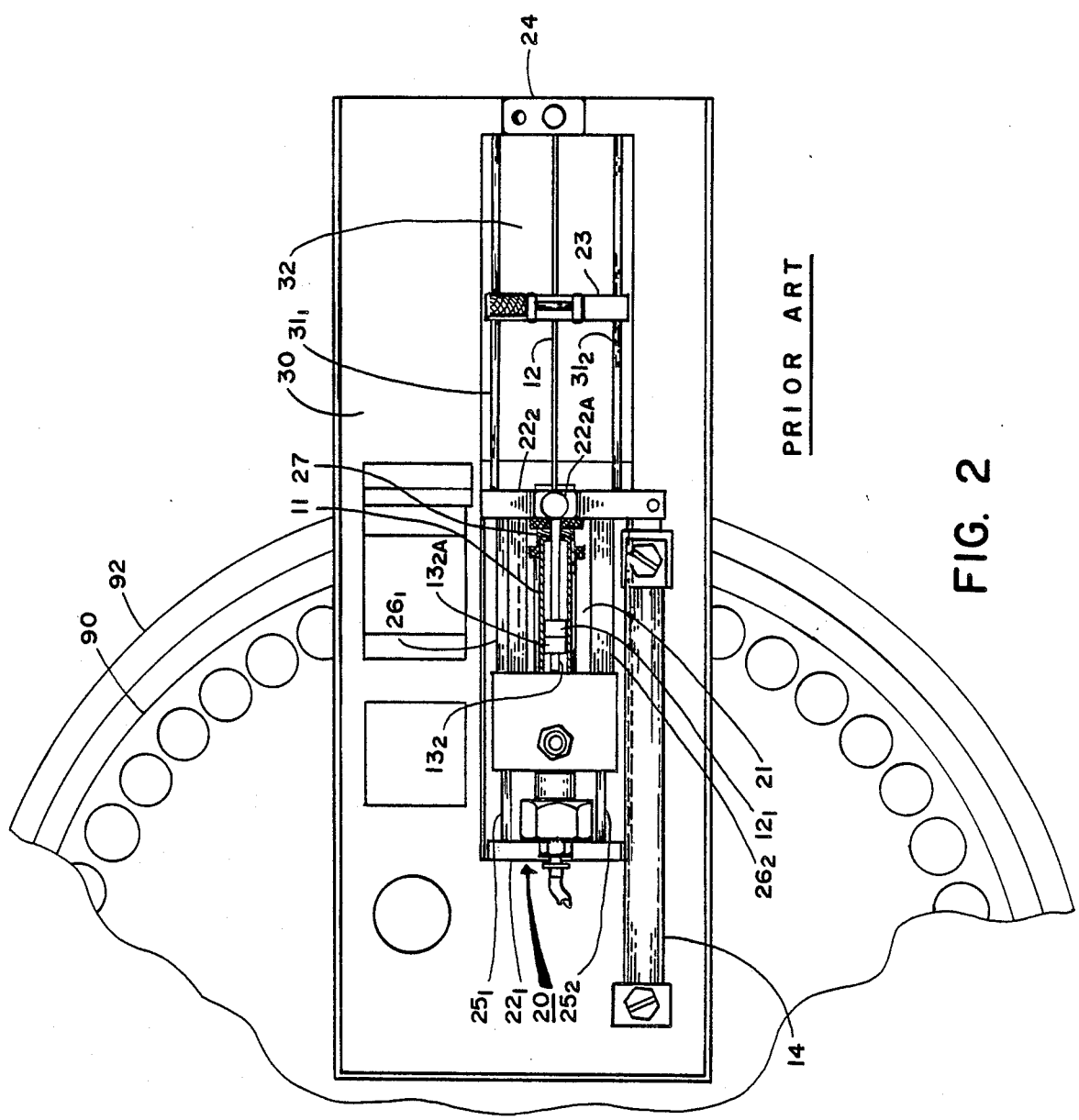
Figure 8:
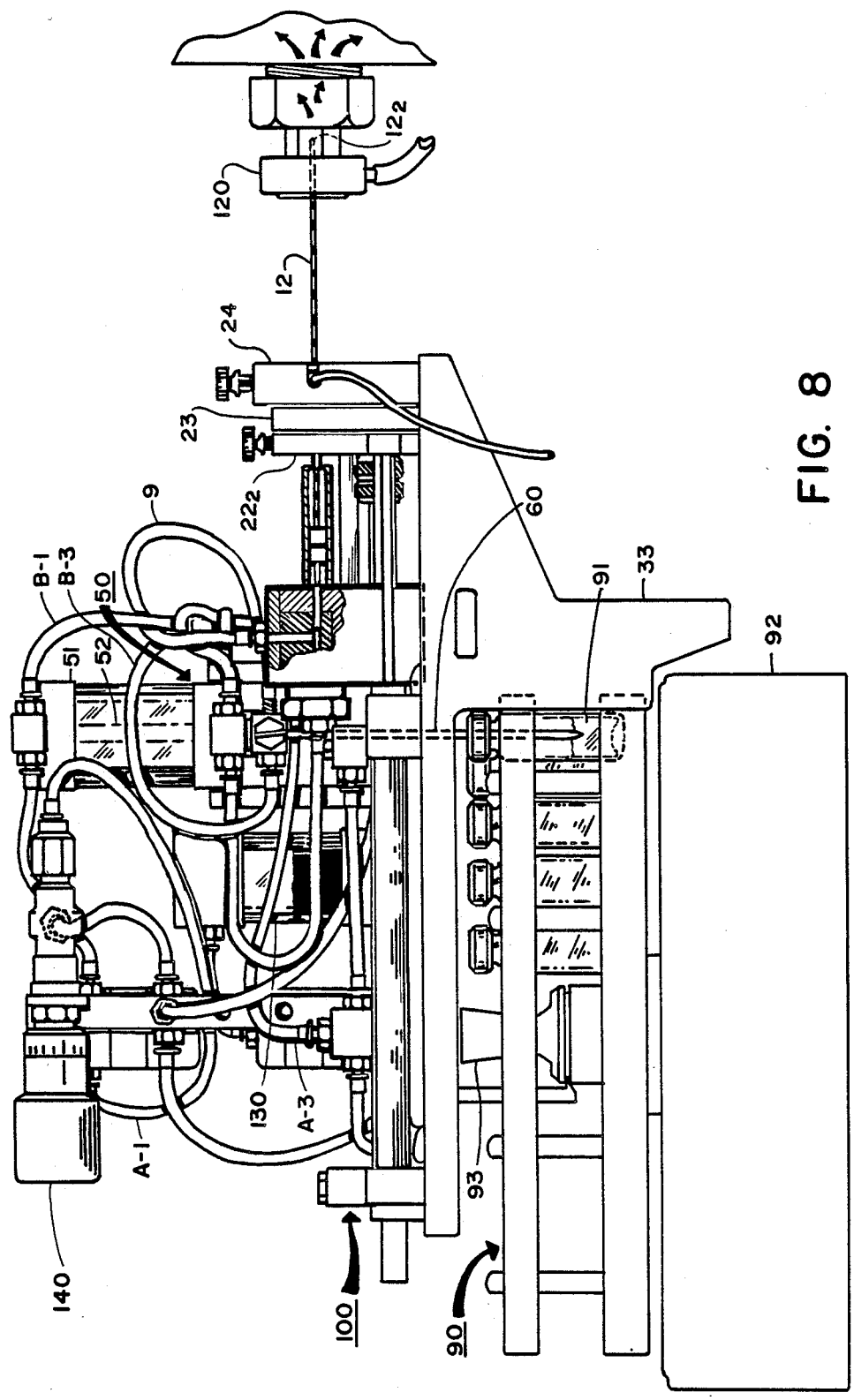
FIG. 8 depicts, via a side elevation view of the automatic fluid injector, initiation of the injection of a fluid specimen from the barrel of the syringe by a continued forward movement of the valve body and barrel portions of the syringe relative to the carriage upon which these elements are transported.
Figure 9:
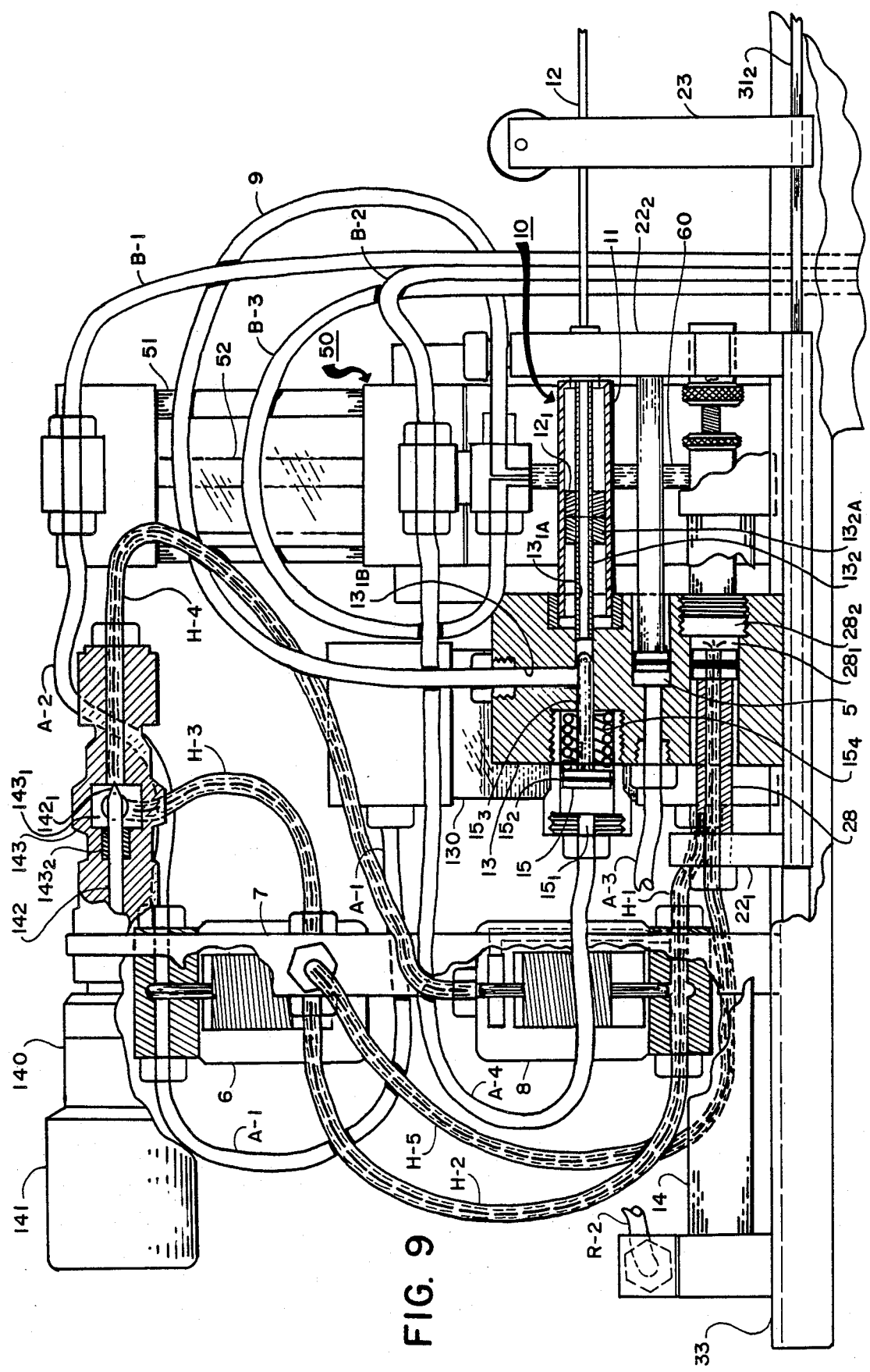
FIG. 9 depicts, via a side elevation view of the automatic fluid injector with appropriate cut-aways, details of the pneumatic and hydraulic systems which actuate said automatic fluid injector.

The syringe, or syringe assembly 10 generally, as best shown by reference to FIGS. 2, 8 and 9, is affixed to and mounted upon a carriage 20, within which the valve 13-barrel 11 sub-assembly is reciprocably movable over a limited preselected, adjustably determined distance; and the carriage 20 is in turn reciprocably mounted upon the platform 30. The carriage 20 is thus mounted upon, slidable, and reciprocably movable upon a pair of parallelly disposed rods or shafts $31_1$, $31_2$ which extend across an open rectangular shaped slot 32 within the horizontally disposed platform 30. The platform 30, as will be noted, is mounted via the vertical support structure 33 above the base 92 upon which the carrousel feed tray 90 is rotatably mounted via a vertical spindle or shaft 93 located at the geometric center of the base 92. The shafts $31_1$, $31_2$ form rails upon which the carriage 20 carrying the syringe, or syringe assembly 10 is reciprocably movable via action of the cylinder-piston unit 14 mounted on the upper surface of the platform 30, located as a superstructure above the base 92.

The syringe, or syringe sub-assembly 10 includes a carriage 20, inclusive of a horizontal oriented floorplate 21, and vertically oriented end members $22_1$, $22_2$ mounted perpendicularly one at each end of the floorplate 21. The outer longer edges on each side of the floorplate 21 is provided with parallelly aligned openings which mate with and slide upon the shafts $31_1$, $31_2$ which run the length of the slot 32. The upper portion of the forward vertical end member $22_2$ is provided with a lock assembly $22_{2A}$ within which the needle 12 can be, and is rigidly secured. A second, protective needle guide mount 23 is located at a spaced distance in front of the forward vertical end member $22_2$, the base of this member being provided with side openings which mate with and slide upon the shafts $31_1$, $31_2$. The guide mount 23 also includes a central shaft (not shown) which extends rearwardly and fits slidably within an elongate central opening on the floorplate 21 of the carriage 20. The protective needle guide mount 23, and an additional fixed needle guide 24 prevents damage to the needle 12 when the carriage 20 is moved forwardly upon the platform 30 over a major portion of the carriage's movement, and then yields to and permits additional continued movement of the carriage 20, the said central shaft being projected inwardly into the central opening within the floor plate 21, as the dispensing end $12_2$ of the needle 12 is inserted within the septum inlet 120.

The carriage 20 is thus reciprocably mounted via rails located atop the platform 30 and can, via action of the cylinder piston unit 14 be oscillated over the length of the rails 31 to project the dispensing end $12_2$ of the needle 12 into the septum inlet 120, and withdraw same. The valve 13-barrel 11 sub-assembly, on the other hand, is also reciprocably movable relative to the needle 12 which, relative to carriage 20 is maintained in a fixed position. The valve 13-barrel 11 sub-assembly is movable within carriage 20 to load the barrel 11 of the syringe with a fluid specimen obtained by the probe assembly 60 from a vial, and then to eject same via the dispensing end $12_2$ of the needle 12 as when the dispensing end $12_2$ of the needle 12 has been inserted into the septum inlet 120. The structure of carriage 20 is essentially as follows: the outer edges of the elongated sides of the vertical end walls $22_1$, $22_2$ mounted on floorplate 21 of the carriage 20 are also provided with parallelly mounted guide shafts $25_1$, $25_2$. The outer lower side edges of the valve 13 are thus provided with openings through which are fitted the guide shafts $25_1$, $25_2$, and tubular stop collars $26_1$, $26_2$ of equal preselected length are fitted on the forward sides of each of the guide shafts $25_1$, $25_2$ such that the valve 13, within the forward base of which the barrel 11 of the syringe 10 is fitted, and extended, is slidably or reciprocably movable over a limited distance thereon. The distance of movement of the valve 13-syringe barrel 11 sub-assembly is defined by the point of impingement of the lower rearward face of valve 13 with the forward face of vertical end member $22_1$, and the point of impingement of the lower forward face of valve 13 with the rearwardly projecting terminal ends of tubular stop collars $26_1$, $26_2$. This distance is set to correspond with the distance between the maximum fill position of the bore of the barrel 11 when the valve 13 is in its extreme rearward position upon the carriage 20, and zero fill position when the valve 13 is in its extreme forward position upon the carriage 20. An adjustable stop 27, or stop member of adjustable length, is located on the forward face of the valve 13 to provide fill settings which are of lesser volume than the maximum. The adjustable stop 27 includes a rearward shaft portion threadably mounted on the forward face of the valve 13. Its forward end includes a knurled, knobbed shaft portion threadably engaged within the forward end of the former such that the effective length of the stop 27 can be shortened, or extended, by rotation of the forward knurled, knobbed shaft portion thereof in one direction or the other to move it outwardly from the fixed shaft portion or inwardly toward the fixed shaft portion of the adjustable stop 27. The lower portion of the forward vertical member $22_2$ is provided with a central opening of relatively large diameter through which the stop 27 can be extended for contact with the vertically oriented end wall $22_2$ to mechanically limit the forward point of movement of the valve 13-barrel 11 sub-assembly to provide a less than maximum fill position. In a filling operation, at zero fill position the adjustable stop 27 is set so that the two syringe seals $12_1$, $13_{2A}$ are in contact, this permitting a fluid specimen to flow through the syringe on the way to the drop counter without filling the bore of the barrel 11. Retraction of the seal $13_{2A}$ away from seal $12_1$ permits the bore of barrel 11 to be filled with the fluid specimen to the extent that the two seals $13_{2A}$, $12_1$ are separated. Full retraction of seal $13_{2A}$ away from seal $12_1$ permits the bore of barrel 11 to be filled to the maximum with the fluid specimen. The full content of the fluid specimen between seals $13_{2A}$ and $12_1$ can then be discharged on the complete closure between seals $13_{2A}$ and $12_1$ by setting the adjustable stop 27 via rotation of the forward knobbed portion thereof in a given direction to its rearward position so that the front end thereof cannot contact the forward vertical end member $22_2$ of the carriage 20 when it is moved forwardly to thrust the dispensing end $12_2$ of needle 12 into septum inlet $12_0$. On the other hand, an accurately measured fluid specimen in lesser amount can be discharged from the bore of the barrel 11 by termination of the forward movement of seal $13_{2A}$ prior to closure with seal $12_1$. This is accomplished by adjustment, via rotation of the forward knobbed portion of the adjustable stop 27 in an opposite direction, so that the front end thereof on forward movement of the valve 13-barrel 11 sub-assembly contacts the forward vertical end member $22_2$ of the carriage 20 when it is moved forwardly, via a preselected, or calculated distance, to thust the dispensing end $12_2$ of needle 12 into septum inlet $12_0$. In general, the bore of barrel 11 is always loaded with a maximum charge of a fluid specimen, this being accomplished by opening the bore of the barrel 11 to its maximum fill position; and this in turn is accomplished by slowly moving the valve 13, from which the barrel 11 of the syringe 10 is extended from a forward position at which the seals $13_{2A}$, $12_1$ are in contact, rearwardly, to its maximum rearward position upon the carriage 20. The opening of the syringe to its maximum fill position is done only after the fluid specimen is flowing from a sample vial through the syringe. The amount of the fluid specimen to be ejected from the bore of the barrel 11 can then be preselected by setting the adjustable stop 27 in the manner described. The valve 13-barrel 11 sub-assembly is moved slowly to its maximum rearward position within the carriage 20 via action of high pressure air injected via line A-3 into a cavity or chamber 5 (FIG. 9) of cylinder-piston unit whose air entrance is located within the rearward face of valve 13. Movement of the valve 13-barrel 11 sub-assembly slowly rearwardly in this manner loads the fluid specimen into the barrel 11 of the syringe via line 9 without the formation of bubbles or foam therein.

Figure 7:
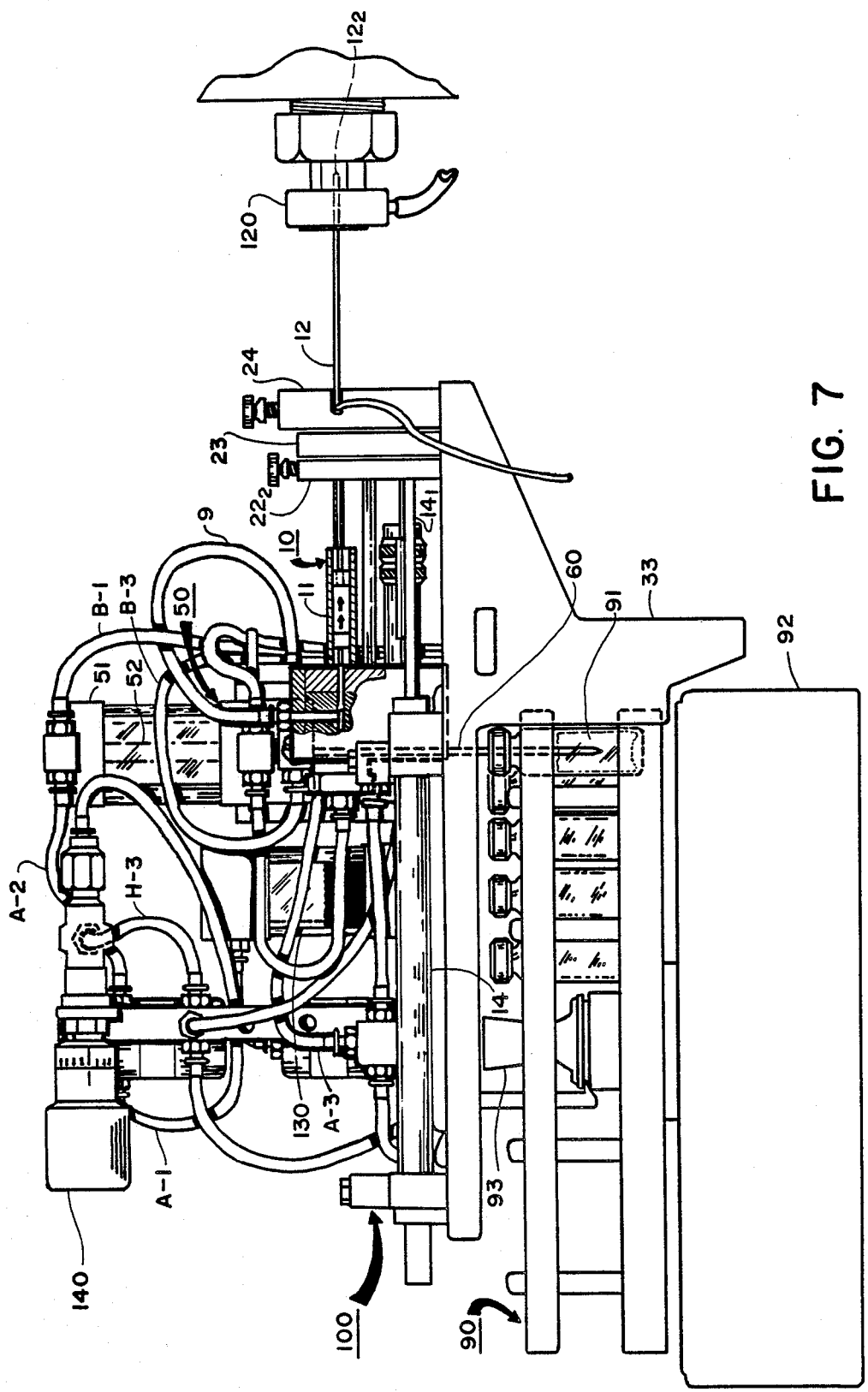
FIG. 7 depicts in partial section, again by means of a side elevation view of the automatic fluid injector, transport of the carriage to its extreme forward position upon the platform, thrust of the dispensing end of the needle of the syringe into a septum inlet, and closure of the valve to cut off the flow of fluid specimen to the syringe from a vial via the probe assembly mechanism.

After filling the barrel 11 of the syringe with a fluid specimen, the next step in the operation of the syringe assembly 10 per se is to transport the syringe assembly across the platform 30 to thrust the dispensing end $12_2$ of the syringe needle 12 into the septum inlet $12_0$ in preparation for the injection of a fluid specimen therein (FIG. 7). This requires movement of the carriage 20 upon which the syringe 10 is transported across the platform 30. The movement of carriage 20 upon the horizonally disposed platform 30 is controlled via the double acting, pneumatic cylinder piston unit 14 mounted upon said platform 30. The forward end of the piston $14_1$ of said cylinder piston unit 14 is thus affixed to an extending side edge of the forward vertical end member $22_2$ of the carriage 22. The carriage 20 is thus moved forwardly by injection of air via line R-2 (FIG. 9) into the rearward side of the cylinder piston unit 14 which causes extension of the piston $14_1$ from within the housing portion of the cylinder-piston unit 14. Initially, the protective forward needle guide mount 23 is carried forwardly, its forward movement ending on contact thereof with the forwardmost needle guide mount 24 whereupon, as the forward movement of the carriage 20 is continued, the central shaft thereof, not shown, is telescoped within the central opening of the floorplate 21 of the carriage. At this point in time the dispensing end $12_2$ of the needle 12 is thrust into the septum inlet $12_0$, and fluid specimen can be injected from barrel 11 by the slow forward movement of the valve 13-barrel 11 sub-assembly within the carriage 20 actuated via hydraulic fluid metered through the fine metering valve 140 (FIG. 9). The carriage 20 is moved in the opposite direction upon the platform 30 by injection of air via line R-3 into the forward end of the cylinder piston unit 14, the piston $14_1$ being withdrawn into the housing of the cylinder-piston unit 14.

The primary function of the valve 13 is to open and close the barrel 11 to the flow of a fluid specimen delivered thereto from a vial via action of the probe assembly 60. When the valve 13 is open, a fluid specimen can be introduced into and passed therethrough to the bore of the barrel 11. When closed, the flow of fluid specimen is interrupted, and on closure to interrupt a previously flowing stream of a fluid specimen a sample of the fluid specimen can be trapped within the bore of the barrel for subsequent injection through the dispensing end $12_2$ of the needle 12. The operation and function of a valved syringe per se as herein employed is described in U.S. Pat. No. 4,044,616 to myself and others, particular reference being made to FIGS. 8 and 9 and to the description thereof at Column 5, lines 32-68 and Column 6, lines 1-17, herewith incorporated and made part of the present disclosure by reference. Referring e.g., to FIG. 9, it will be observed generally that the rearward end of the barrel 11 is snugly fitted, sealed, and contained within the forward face of the valve 13 and movable therewith. The valve 13 is one provided with an on-off position, or one which can be controlled, i.e., opened and closed, in response to a signal, especially an electric signal. The valve 13, as best illustrated by reference to FIG. 9, is constituted of an outer body or block within which is provided a chamber (suitably lined with packings, not shown) formed by a pair of intersecting openings, a horizontal opening $13_{1A}$ and a vertically oriented opening $13_{1B}$ communicated therewith, the latter providing a connecting conduit through which a fluid specimen can be conveyed via line 9 from the probe assembly 60 of the injector-feed assembly 50 into the barrel 11 of the syringe. The forward portion of the horizontal opening $13_{1A}$ provides a nozzle outlet and connecting channel through which a fluid specimen can be conveyed via vertical opening $13_{1B}$ into the syringe barrel 11, and the opening $13_{1A}$ as a whole further provides a means, with piston 15, for opening and closing the vertical opening $13_{1B}$ to the flow of a fluid specimen therethrough; or, in other words, a mechanism for opening and closing the valve 13.

The chamber of valve 13 is communicated with a large diameter opening axially aligned upon and continuous with opening $13_{1A}$, the large diameter opening containing a pneumatically actuatable piston 15, the function of which is to open and close the valve 13 in response to an actuating signal, pressurized air entering the chamber via gas entry port $15_1$ to close the valve. The piston 15 thus includes a piston head $15_2$ and stem $15_3$, the former of which lies within said large diameter opening, the latter of which lies within opening $13_{1A}$ to provide the closure element per se of the valve. The piston head $15_2$, with its circumferential o-ring seals, is snugly fitted within the large diameter opening which is communicated with the chamber of the valve 13, and the stem $15_3$ extends into the opening $13_{1A}$. The piston 15 can, e.g., be biased in closed position by a helical coil spring $15_4$ seated between an outer face of the valve body and inner face of the piston head $15_2$ such that entry of a pressurized gas, e.g., air or nitrogen, via said gas entry port $15_1$ into the valve body will close the valve 13. Thus, the pressure exerted by the helical spring $15_4$ will be overcome and the valve closed by advancing stem $15_3$ into the opening $13_{1A}$ to cut off the flow of a fluid specimen introduced via line 9 to fill the bore of the barrel 11. Conversely, when no pressurized gas is admitted, or gas is cut-off to the gas entry port $15_1$ the helical spring $15_4$ will be re-extended and will cause retraction of the stem $15_3$ from within the opening $13_{1A}$ to unblock the vertical side opening $13_{1B}$ to permit the flow of a fluid specimen via line 9 into the bore of the barrel 11.

(B) The purpose of the injector feed assembly 50, with its probe sub-assembly 60, is to pick up a fluid specimen from septum covered vials 91 carried and serially positioned beneath the probe assembly 60 by the carrousel feed tray 90, to withdraw and convey fluid specimen from a vial so positioned to the barrel 11 of the syringe 10. The injector feed assembly 50 includes means, suitably a double acting cylinder piston unit 51, for vertical reciprocation of the probe assembly 60 with which it is an integral part. The lower terminal end of the shaft, or piston 52 of the cylinder piston unit 51 thus carries a reciprocable hollow probe, or probe assembly 60 which can be projected through the septum of a septum covered vial 91 to withdraw or pick up a fluid specimen therefrom for transfer to the barrel 11 of the syringe 10.

Figure 3:
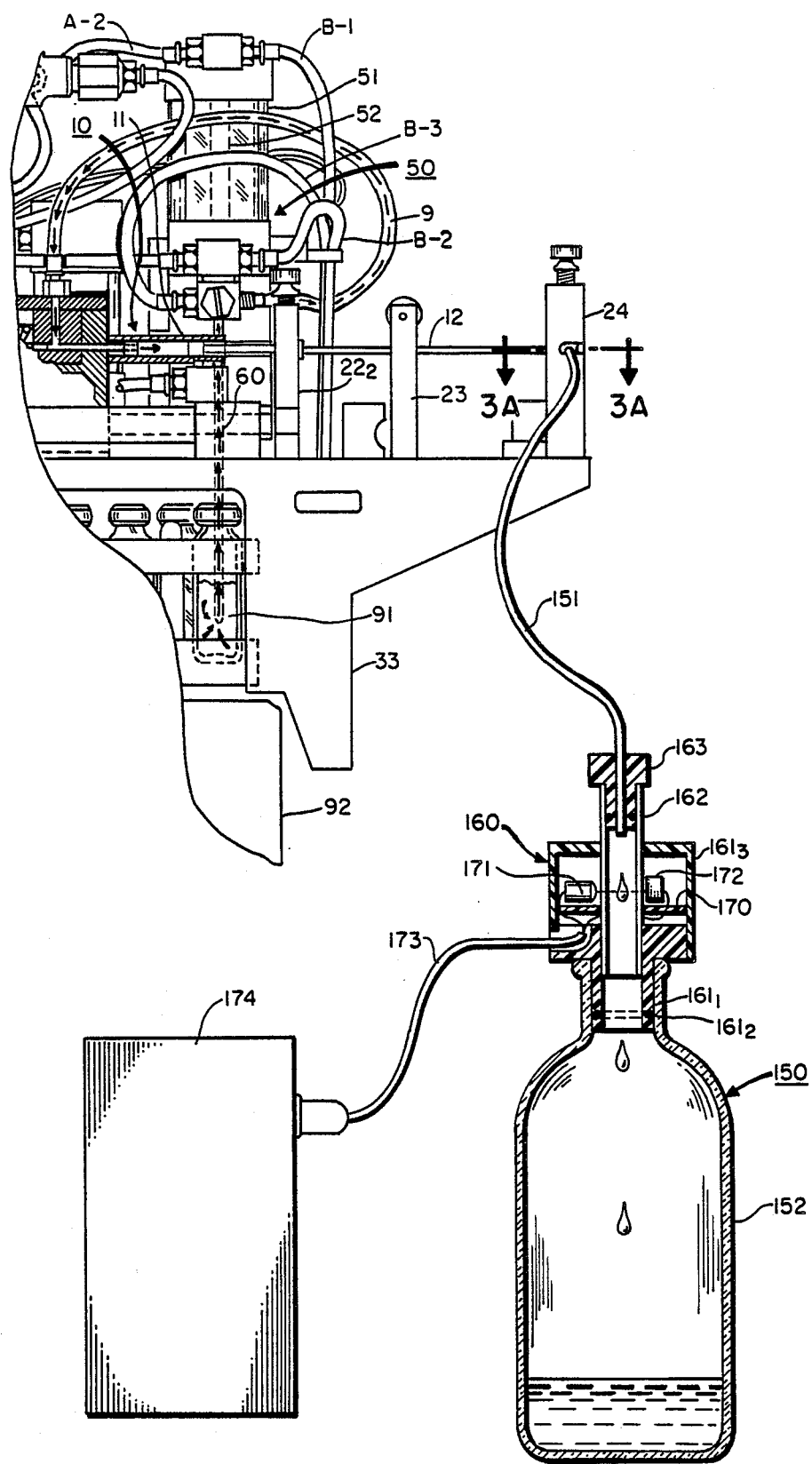

The details of the injector feed assembly 50 is first discussed with reference to FIGS. 1 and 3, and details of the probe assembly 60 are given by reference to FIG. 6. In FIG. 1 the probe assembly 60 is held in raised position, the piston 52 being withdrawn within the housing or barrel of the cylinder piston unit 51. In FIG. 3 the probe assembly 60 is shown after having been lowered to pierce the septum of a vial 91 for withdrawal of a fluid specimen therefrom for conveyance to the barrel of the syringe 10. The cylinder piston unit 51 per se is conventional. The principle components of the injector feed assembly 50 includes the piston 52 of the cylinder piston unit 51, which carries a probe assembly 60 which can be vertically reciprocated by alternate injection of air, or other pressurized fluid, against the head of the piston contained within the housing or barrel portion of the cylinder piston unit 51. The piston 52, and consequently the probe assembly 60, is reciprocated, first by injection of air via line B-1 into the top end of the housing of the cylinder piston unit 51 to move the piston 52 downwardly, and alternatively into the lower end of the housing via line B-2 to move the piston 52 upwardly. Thus, the septum of a vial 91 transported into position, or on station, beneath the probe assembly 60 is penetrated by downward projection of the probe assembly 60 carried by piston 52 when air is injected via line B-1 into the upper end of the housing of the cylinder piston unit 51. It is withdrawn from a vial 91 via injection of air via line B-2 into the lower end of the housing of the cylinder piston unit 51.

The structural details of the probe assembly 60, and its function, are best described and illustrated by reference to U.S. Pat. No. 4,044,616, supra, specific reference being made to FIG. 7 and the description thereof at Column 8, lines 53–68 and Column 9, lines 1–3 herewith incorporated by reference. The operation of the probe assembly 60, and its function, will be understood by continued reference to FIG. 3, and FIG. 6. The lower end of probe assembly 60, as shown in FIGS. 3 and 6 is projected into a vial 91 which contains a fluid specimen which is to be delivered to the barrel 11 of syringe 10. The probe assembly 60 per se, as shown best by reference to FIG. 6, is constituted of a pair of concentrically mounted hollow needles; an inner needle $61_1$ contained within a larger needle $61_2$. An annulus between the inner needle $61_1$ and outer needle $61_2$ provides an internal conduit within which a gas, suitably air, under low pressure can be transmitted through an inlet as via line B-3 through a connecting port 62, the gas entering vial 91 via the exit port $61_3$. Since the gas cannot escape from the vial due to the presence of the septum $91_1$, which is held tightly atop the vial by a screw cover $91_2$, the fluid contents of the vial are pressurized by the entering gas, and fluid specimen is forced into the entry port $61_4$, the fluid specimen ascending through the bore of needle $61_1$ and exiting the connecting tubing 9 whereupon it flows through the valve 13 on opening into the barrel 11 of syringe 10

(C) The function of the carrousel feed tray 90 is to transport fluid specimen filled vials in seriatim one behind the other to a location for pick up and transport of the fluid contents thereof to the syringe barrel 11 by the injector feed assembly 50. The injector feed assembly per se can be of virtually any type, or design as described e.g., in U.S. Pat. No. 3,754,443, U.S. Pat. No. 3,824,859, U.S. Pat. No. 3,885,438, U.S. Pat. No. 3,940,995. In a preferred embodiment, as described herein, a carrousel feed tray 90 is provided for conveying a plurality of fluid specimen-containing vials 91. It is constituted of a rotary table containing, or which can contain, a plurality of fluid specimen containing vials 91; the table being rotated about a spindle or shaft 93 located at the geometric center of the base 92. As the vials 91 are serially moved into position beneath the probe assembly 60 of the injector feed assembly 50, the probe 60 is thrust downwardly so that the pointed or tapered end of the outer needle $61_2$ penetrates the septum $91_1$ of a vial in an initial step in preparation for pick up and transport of a fluid specimen to the barrel 11 of the syringe 10.

Figure 3A:
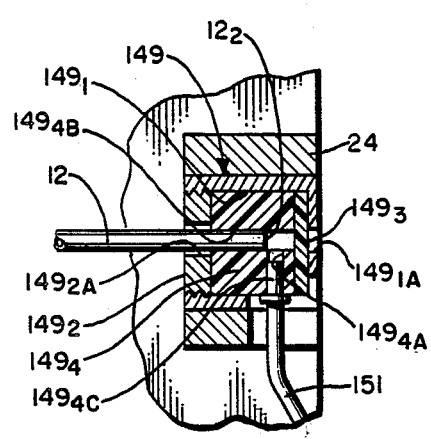
Figure 4:
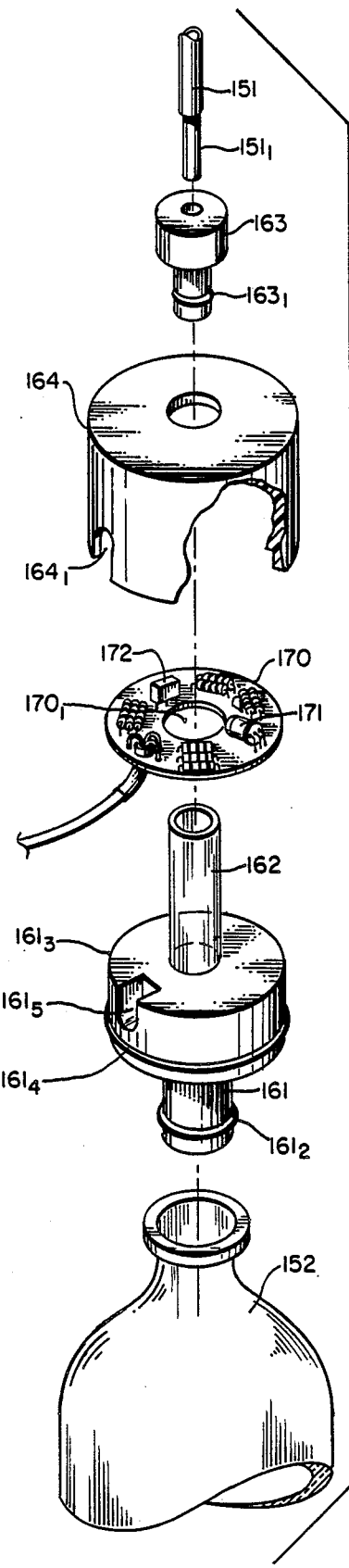
FIG. 4 is an exploded view of the automatic drop counter means.

(D) The automatic drop counter 150 and its function are best described by direct reference to FIGS. 3, 3A and 4. After the septum of a vial 91 has been pierced, and the vial 91 pressurized, the fluid specimen ascends via the probe assembly 60 and line 9 to enter into the barrel of the syringe 11 via the open valve 13. The fluid specimen exits the syringe 11 via the dispensing end of needle 12, which as depicted in FIGS. 3, 3A lies within a fluid diversion valve 149 located within the forwardmost needle guide mount 24. The fluid diversion valve 149, shown by direct reference to FIG. 3A, is used to carry away via line 151 a portion of the fluid specimen used for cleaning and purging the fluid injector, or syringe. Referring specifically to FIG. 3A, the fluid diversion valve 149 is constituted of a cup-like member $149_1$ the front end of which is closed but for a central opening $149_{1A}$. The rearward end of the cup-like member $149_1$ is internally threaded for threadable engagement with an externally threaded open centered cap $149_2$. The cup-like member $149_1$, and cap $149_2$ are generally constituted of metal, e.g., copper, or brass. Within the cup-like member $149_1$ there is contained a a diaphragm, or septum $149_3$, and behind the diaphragm, or septum $149_3$, in contiguous relation therewith, there is contained a resilient tubular member $149_4$, preferably constituted of a plastic or plastic-like material, suitably a semi-rigid or rigid plastic such as polytetrafluoroethylene (Teflon). The tubular member $149_4$ is provided with a lateral opening $149_{4A}$ which communicates with the axial opening $149_{4B}$, and the axial opening $149_{4B}$ is coaxially aligned upon the central front opening $149_{1A}$ of the cup-like member 149 and central cap opening $149_{2A}$. The septum $149_3$ and resilient tubular member $149_4$ are positioned and held in place by the cap $149_2$, and also a tubular fitting $149_{4C}$ contained within lateral opening $149_{4A}$. The tubular fitting $149_{4C}$ provides a means for connection of a flexible base 151. It will thus be seen that when the dispensing end of needle 12 has been projected through cap opening $149_{2A}$ to lie within the tubular opening $149_{4B}$, upstream of the septum $149_3$, a fluid-specimen flowing from the dispensing end $12_2$ of the needle 12 will flow via lateral opening $149_{4A}$, tubular fitting $149_{4C}$ and tubing 151 to the automatic counter 150.

The automatic fluid counter 150 is constituted of a container, preferably a necked slop bottle 152, upon the upper neck portion of which is supported a stopper, or stopper assembly 160 within which is provided an element 170 on which is mounted a light emitter 171, a detector or sensor 172 and electrical circuitry for counting the drops of fluid specimen conveyed to the slop bottle 152 as droplets, and electrical means for responding to a preselected number of drops delivered thereto to activate mechanism for closure of valve 13 to interrupt the flow of fluid specimen from the needle 12. The stopper assembly 160 includes generally a plug, or stopper per se 161, a cap 164 and an element 170 contained therein which contains the electronics. The stopper per se of the stopper assembly 160 is constituted of a lower reduced diameter portion $161_1$ which is projected into the neck of the bottle 152, mates with and is sealed thereto; suitably with the aid of an O-ring $161_2$. The upper large diameter portion $161_3$ of the stopper 160 is provided with a straight, transparent tubular member 162 within the top which is provided a tubular guide member or seal 163. The axial opening of the seal or tubular guide member 163 is fitted with a tubular segment $151_1$ to which the tube 151 is adjoined (FIG. 4). Suitably, the lower, small diameter end of the tubular guide member 163 is provided with an O-ring $163_1$ to provide a better seal within tubular segment 162. An open centered cap 164 provided with a relatively large diameter internal opening mates with and caps the upper large diameter portion $161_3$ of the stopper 161, sufficient space being left between the upper inside face of cap 164 and the top face of the upper large diameter portion $161_3$ of the stopper 161 to provide a chamber for containment of the element 170 which contains the emittor 171, detector 172, and electrical circuitry.

The element 170 is of washer-like shape; round, open centered and both of its faces are substantially flat. The cable 173 extending therefrom is passed through an opening formed by a notch $164_1$, in cap 164 and notch $161_5$ in the stopper 161 (FIG. 4). The upper face, at one side of the central opening $170_1$, is provided with a light emitting device, or light emittor 171. The upper face of the element 170, on the opposite side of opening $170_1$, is provided with a light detector, or sensor 172. The light emittor 171 and detector 172 are in electrical communication one element with the other, a terminal connection being extended through the electrical cable 173 for connection with a control box 174. A beam of light continuously emitted by the emittor 171 is thus focussed upon the detector 172, the beam of light passing through tubular element 162, with the beam of light being interrupted by each drop or bubble of a fluid specimen which falls through the opening $170_1$. Each passing drop is electronically counted, input via the electrical circuit contained in cable 173 to a counter within a control box 174, and in accordance with a preselected count (or preselected period where no drops are counted, where desirable for reason of safety) a computer contained within the control box 174, or operative therewith, closes the valve 13 to interrupt the flow of fluid specimen to the syringe.

Figure 5:
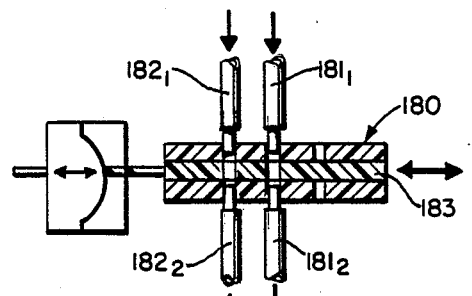
FIG. 5 depicts another type of fluid injector means for the delivery of a calibrated, accurately measured specimen of fluid to an automatic drop counter means.

By reference to FIG. 5, there is depicted an alternate device, or apparatus, by virtue of which an accurately measured amount of a fluid specimen can be injected into the septum inlet of a analytical instrument, e.g., a G.C. Thus, a fluid specimen can be flowed from a supply source (not shown) via line $181_1$ through the open port of a multi-port valve 180, the fluid specimen exiting the valve 180 via line $181_2$ where it is delivered to automatic drop counter means as described in connection with FIGS. 3 and 4. Simultaneously, carrier gas from a supply source (not shown) is continuously supplied via line $182_1$ and flowed through an open port of the multi-port valve, or slide valve 180, exiting therefrom via line $182_2$. The opening in the slide 183 through which the fluid specimen is passed is calibrated such that, on activation and movement of the slide 183 to the position formerly occupied by the carrier gas slide opening via signal from the automatic drop counter an accurately measured portion of fluid specimen can be input to the septum inlet of the analytical instrument.

Reference is again made to the instrument depicted, and described by reference to FIGS. 1-4 and 6-9. The apparatus combination includes means, preferably both pneumatic and hydraulic means, for powering the operations of the (A) syringe, or syringe assembly 10, and (B) the injector feed assembly 50 to assure optimum time periods, and optimum performance for each portion of the total cycle of operation. Preferably the carriage 20 is oscillated across the platform 30 via pneumatic means, suitably via use of the double-acting pneumatically activated cylinder piston unit 14. High pressure air can thus be used to rapidly move the piston $14_1$ in one direction to drive the carriage 20 in its forward direction to insert the dispensing end $12_2$ of the needle 12 into the septum inlet 120, and in an opposite direction to retract the needle 12 by withdrawal of the piston $14_1$ to reverse the direction of movement of the carriage 20. High pressure air is also employed to lower and raise the probe assembly 50 via injection of air into the top end via line B-1 and lower end via line B-2, respectively, of the cylinder piston unit 51 of the injector feed assembly 50. Air, at relatively high pressure is also injected via line A-1 into the top of a hydraulic reservoir 130 to provide the desired pressure upon the oil, and air can be used to open and close the valve 13, viz., via air fed through line A-4 to the piston unit 15 to close the valve 13, and the cutting off of air thereto to open the valve 13. Low pressure air can be passed via line B-3 into the probe assembly 60 to pressurize a vial 91 for conveying a fluid specimen to the barrel of the syringe. Metered high pressure air is also preferably employed via injection thereof through line A-3 into the piston cavity 5 to retract the valve 13-barrel 11 sub-assembly to fill the barrel of the syringe with a fluid specimen supplied via the injector feed assembly 50.

A hydraulic reservoir 130, precision flow needle control valve 140, hydraulic piston units and leads thereto as hereinafter defined constitute the heart of the hydraulic system. Reference is best made to FIG. 9. The precision flow needle control valve 140 is constituted generally of a knurled knob portion 141 rigidly affixed to a shaft 142 which is threadably engaged with, and extended through an axial opening within a tubular body 143. The tubular body 143 of the needle control valve 140 contains a chamber $143_1$, a conical shaped forward end and rearwardly placed packing $143_2$ through which the tapered or pointed end $142_1$ of the shaft 142 is extended. The tapered end $142_1$ of the shaft 142, when located in a position sufficiently rearwardly of the conical shaped inlet to chamber 143 provides a relatively large opening for the input of hydraulic fluid via hydraulic inlet line H-4, and conversely when the tapered end $142_1$ of the shaft 142 is closely located to the conical shaped inlet to chamber 143 a relatively small opening restricts the flow for the input of hydraulic fluid via hydraulic inlet line H$_4$. Hydraulic fluid from reservoir 130 is thus metered by rotation of the scaled knob 141 in one direction to project the tapered needle end $142_1$ of shaft 142 into the restricted passageway of tapered cross-section to restrict oil flow from the input side to the output side of the needle valve 140, and in the opposite direction to withdraw the needle end $142_1$ of the shaft 142 from the conical passageway to permit greater flow from the input side to the output side of the needle valve 140. A metered flow of hydraulic fluid is used to close the valve 13-barrel 11 sub-assembly upon the needle 12 to inject a fluid specimen from the barrel 11, after closure of valve 13 with high pressure air.

An operating cycle is conveniently described again by direct reference to FIGS. 1-4 and 6-9, these figures taken in sequence depicting the pick up of a fluid specimen from a septum covered vial and delivery thereof to the barrel of the syringe, or syringe assembly 10, and injection of a preselected quantity of the fluid specimen into the inlet of an analytical instrument, as follows:

(a) Referring first to FIG. 1, the probe assembly 60 of the injector feed assembly 50 is shown in elevated, or raised position, the piston 52 being withdrawn into the housing or barrel of the cylinder piston unit 51. A vial 91 has been delivered to a location beneath the probe assembly 60 via rotation of the carrousel feed tray 90 (via means not shown), on which is carried a plurality of vials 91. The carrousel feed tray 90, at this point in time is now motionless.

The carriage 20, as shown by reference to FIGS. 1 or 2, is in its extreme rearward position upon the horizontal platform 30, the piston 52 of the cylinder piston unit 51 being withdrawn upwardly with its housing. The valve 13 is in its extreme forward position on the carriage 20. In this position, it will be observed that the forward face of the block which forms the valve 13 rests against the tubular collar stops $26_1$, $26_2$ and the forward face of the tubular seal $13_{2A}$ of the projecting nozzle stem $13_2$ abuts the rearward face of the tubular seal $12_1$ on the rearward end of needle 12. The interface of the two tubular seals $13_{2A}$, $12_1$ is at the point indicative of the maximum fill position, though at this point in time there is no space for a fluid specimen within the bore of the barrel 11. The valve 13 at this point in time is closed. The needle 12 is in a fully retracted position.

In this position, hydraulic fluid has thus just closed the syringe via forward movement of the valve 13-barrel 11 sub-assembly within the carriage 20. Hydraulic fluid from the body of fluid in reservoir 130, pressurized by air introduced into the vessel above the fluid body via line A-1, was thus transferred via lines H-1, past solenoid 8 to H-2, and through the T-frame 7 via line H-5 into the nozzle inlet 28 at the lower side of the valve 13. Pressurized hydraulic fluid entering nozzle inlet 28, rigidly affixed to the vertical end wall $22_1$, thus fills the chamber $28_1$ and pushes the valve 13-barrel 11 sub-assembly to its extreme forward position within the carriage 20.

The setting on the adjustable stop 27 to deliver the desired quantity of a fluid specimen into the septum inlet 120 can be made at this time. Thus, the adjustable stop 27, the rearward terminal end of which is threadably engaged with a large antechamber $28_2$ forward of chamber $28_1$ can be moved inwardly or outwardly, respectively, to limit or extend, as desired, the distance of movement of the valve 13-barrel 11 sub-assembly within the carriage 20. Thus, outward extension of the adjustable shaft 27 shortens, and limits the distance of travel; travel of the valve 13-barrel sub-assembly 11 being ended by physical contact of the terminal end of shaft 27 with the front guide support 24. When contact occurs prior to closure of seals $13_{2A}$, $12_1$ less than the maximum amount of the fluid specimen is discharged from the barrel of the syringe. Discharge of the maximum amount of the fluid specimen is accomplished when the length of the adjustable stop 27 is set to permit closure of seals $13_{2A}$, $12_1$, this occurring when the valve 13-barrel 11 sub-assembly travels to its extreme forward position within the carriage 20 at the time of injection of a fluid specimen into septum inlet 120.

(b) The probe assembly 60 of the injector feed assembly 50, with its concentric needle assembly 61, is projected downwardly, pressurized air being injected via line B-1 into the upper end of the cylinder piston unit 51 to move the shaft or piston 52 downwardly; the piston 52 carrying with it the probe assembly 60.

Air fed into the top of the hydraulic reservoir 130 via line A-1 is now turned off.

Figure 6:
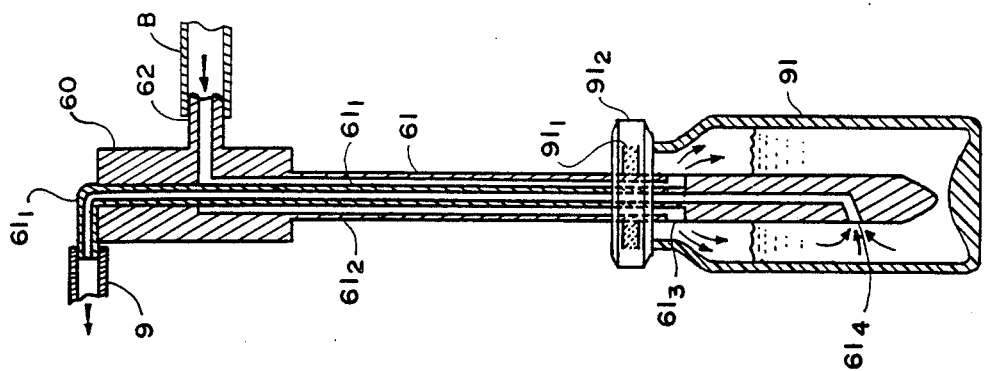
FIG. 6 is an enlarged fragmentary view which gives some further details of the probe assembly per se.

Reference is made to FIGS. 3, 6 and 9. The terminal end of the probe assembly 60 near the bottom of its stroke penetrates the septum of a vial 91, a pressurized gas is injected via line B-3 and inlet 62 into the annulus between the pair of probe needles $61_1$, $61_2$, the gas exiting via the opening $61_3$ to pressurize the inside of a vial 91. The fluid specimen of the vial 91, under pressure, is forced via opening $61_4$ into the inner probe needle $61_1$ whereupon it is conveyed via line 9 to the open valve 13 (earlier opened via cutting off the flow of pressurized air via line A-4 to cause retraction of the valve stem $15_3$ away from the lateral opening $13_{1B}$).

Air from a solenoid D (not shown) now causes air to be transmitted via a line (not shown) into an end of the cylinder piston unit 14, not activating the cylinder piston unit 14 in this instance since the piston $14_1$ of this unit is already retracted. The air transmitted through line A-3 into cavity 5 begins to retract the valve 13-barrel 11 sub-assembly within the carriage 20, this movement of the valve 13-barrel 11 sub-assembly ending with the syringe in its standard load position.

As the valve 13-barrel 11 sub-assembly moves rearwardly upon the carriage 20 the interface between the two seals $13_{2A}$, $12_1$ gradually widens and forms an opening within the barrel which is filled with fluid specimen injected via line 9 into the open valve 13. The valve 13-barrel 11 sub-assembly is moved rearwardly, and the opening bore of the barrel 11 is filled. The filling of the barrel continues until, e.g., the lower rearward face of the valve 13 comes into contact with the rearward vertical wall $22_1$ of the carriage 20. At this point in time the rearward interface of the seal $12_1$ of needle 12 is at a zero reading, the distance between the interfaces of the two seals providing maximum fill. During the filling procedure a vial 91 from which a fluid specimen is being withdrawn remains under pressure, this pressure also being applied to the syringe to aid in suppressing the formation of bubbles. During this period of rearward movement of valve 13, it will be additionally noted that the needle 12 is maintained in a fixed position; the needle 12, with its rearward seal $12_1$ remaining stationary. The valve 13-barrel 11 sub-assembly and the end seal $13_{2A}$ of nozzle $13_2$ is thus moved relative thereto.

As the barrel of the syringe 11 is filled, the fluid specimen also fills the bore of the needle 12, flows therethrough, and exits the dispensing end of the needle 12. The dispensing end of the needle 12, it will be observed by particular reference to FIGS. 3 and 3A, lies within the fluid diversion valve 149. On exit of the fluid from the dispensing end $12_2$ of needle 12 the fluid is introduced into the fluid diversion valve 149 and conveyed via line 151 to the automatic drop counter 150. As drops of fluid fall through the tube 162 between the light emittor 171 and detector 172 they are individually counted and, when a preselected number of drops have fallen into the waste bottle 152 the valve 13 can be actuated and closed. The system is thus controlled in response to actual volume flow of the fluid specimen from a vial through the syringe rather than a discrete time period. The period of time for handling each specimen varies dependent on the actual viscosity of the fluid specimen. Thus, the drops of fluid are counted, and when the predetermined number of drops have fallen— viz. with the last drop—the automatic counter via its electrical input to the control box 174 causes actuation of solenoid B (not shown) which comes "on" to inject air via line A-4 to the piston unit 15 to close valve 13, and block any further flow of fluid specimen via line 9 into the syringe.

(c) Reference is made to FIG. 7. The carriage 20 is now driven forwardly relatively rapidly via activation of a solenoid C (not shown) which is turned "on" to cause the injection of air via line A-3 into the rearward end of the cylinder piston unit 14, the piston $14_1$ being projected outwardly from its housing. The needle 12 is guided along its path, and protected from bending by the protective needle guide $22_2$ which moves forward with the carriage 20, upon which it is mounted, until it contacts the forward needle guide 23, and thereafter, as forward movement of the carriage 20 is continued, the shaft portion of the needle guide $22_2$ telescopes within the floorplate 21 of the carriage 20, further continuously protecting and guiding the needle 12 as it does so. The movement of the carriage 20 stops after the vertical front wall $22_2$ of the carriage 20 contacts the forward needle guide 23, and the forward needle guide 23 contacts the forwardmost needle guide 24. At this point in time, the dispensing end $12_2$ of the needle 12 is inserted within the inlet 120.

(d) Reference is made to FIG. 8. The valve 13, yet closed, is next brought slowly forwardly within the carriage 20 the barrel 11 telescoping upon the seal end of needle 12 to displace fluid from the bore of the barrel. Solenoid 6 is switched "on" to supply air to the top of reservoir 130 (but solenoid 8 remains inactivated to divert hydraulic fluid through the needle valve 140 via line H-4).

Metered hydraulic fluid leaving the needle valve 140, passes through lines H-3 and H-5 to enter the bottom of the valve 13 via nozzle inlet 28 to initiate movement of the valve 13-barrel 11 sub-assembly such that an accurately measured quantity of the fluid specimen is, in this manner injected from the barrel 11 and through this dispensing end of the needle 12. If less than a full barrel of the fluid specimen is to be injected, the adjustable stop 27 can be set to control the forward distance of movement of the valve 13-barrel 11 sub-assembly upon the carriage 20. To inject the full contents of the barrel 11, the interface of the nozzle seal $13_{2A}$ is brought all the way forward to the zero fill position, and into contact with the rearward interface of the seal $12_1$ of needle 12 To deliver a lesser accurately measured quantity of the fluid specimen from the barrel 11 the adjustable stop 27 is set such that the forward end thereof will impinge upon forward vertical carriage wall $22_2$ prior to closure of seals $13_{2A}$, $12_1$. The amount of fluid delivered via the dispensing end $12_2$ of the needle 12 into the inlet 120 is thus directly determined by the amount of fluid displaced by the seal end of the needle 12 as the barrel 11 is moved relative thereto, and this can be adjusted by this, or various other mechanical means known to the art. Injection of an accurately measured quantity of a fluid specimen thus accomplished, if desired the valve 13 can again be opened, and the flow path between the probe assembly 60 and needle 12 readily cleaned as with a solvent, or solvents, and dried, e.g., with air.

(e) To ready the instrument for the next cycle of operation, solenoid D (not shown) comes "on" at exactly the same time that solenoid C (not shown) is turned "off," this actuating the cylinder piston unit 14 causing it to retract the carriage 20. On actuation of solenoid D (not shown) air is injected into the forward end of cylinder-piston unit 14 to cause withdrawal of piston $14_1$ into its housing. The carriage 20 is thus repositioned in its most rearward position upon the platform 30, as shown with reference to FIG. 1.

Solenoid A (not shown) now is inactivated, air being injected via line B-2 into the bottom of the cylinder piston unit 51 to retract the probe assembly 60 of the injector feed assembly 50, and return same to its raised position.

At the same time solenoid D (not shown) is activated, solenoid G (not shown) is activated to allow the valve 13-barrel 11 sub-assembly to be retracted to load position in a rapid unmetered manner, as heretofore described, and the air effecting the retraction of the valve 13-barrel 11 sub-assembly is also directed via line A-3 into cavity 5. Solenoids B, D and G are now inactivated, leaving the instrument ready to begin a new cycle with rotation of carrousel tray 90 to place a new vial in sample position.

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the fluid injector is normally constructed of glass, or a plastic or plastic-like material. The barrel is generally scribed with indicia representative of the volume of the bore. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or plastic-like materials, such as natural or synthetic rubbers can also be employed.

The fluid injector sub-assembly (except for the barrel), the injector feed assembly, particularly the needle and probes, the piston units, and the like, are preferably constructed of metals, e.g., ferrous metals such as iron, iron alloys, steel, stainless steels, and the like; or such metals as aluminum magnesium, brass, copper, bronze, chrome, alloys of these and other metals, and the like.

It is apparent that various changes, such as in the shape, or the absolute or relative dimensions of the parts, materials used, and the like, as well as the suggested mode or particular sequence of withdrawing or delivering fluid specimens, can be made without departing the spirit and scope of the invention, as will be apparent to those skilled in this art.

Having described the invention, what is claimed is:

1. In an apparatus combination useful for the injection of a small accurately measured quantity of a fluid specimen into an inlet of an analytical instrument, said apparatus being characterized as one which includes means for the pickup of fluid specimen from a supply source, a calibrated chamber wherein at least a portion of the fluid specimen is charged to fill the chamber and overflow a portion of the fluid specimen as droplets from the chamber, closure means for closing the calibrated chamber to trap an accurately measured quantity of the fluid specimen therein, and means for injection of the measured quantity of fluid specimen into the inlet of said analytical instrument, the improvement comprising drop counting means for monitoring and counting a preselected number of the drops of the fluid specimen overflowing said chamber, and means responsive to said drop counting means for interrupting the flow of fluid specimen from said supply source to trap said fluid specimen within said calibrated chamber prior to injection of the measured quantity of the fluid specimen into the inlet of said analytical instrument.

2. The apparatus of claim 1 wherein the supply source of the fluid specimen is a feed tray carrying at least one septum covered vial filled with the fluid specimen, the means for pickup of the fluid specimen from said vial is a feed injection assembly inclusive of a probe comprised of a pair of hollow needles, a first of which conveys a pressurized gas into the vial while the second needle thereof transports the fluid specimen driven therein by the pressurized gas, and the calibrated chamber is a syringe having a barrel and needle portion through which the fluid specimen is flowed and then discharged from a dispensing end of the needle portion.

3. The apparatus of claim 2 wherein the feed tray carries a plurality of said vials, and the probe picks up fluid specimen from the vials in seriatum.

4. The apparatus of claim 1 wherein the calibrated chamber is a syringe having a barrel and needle portion through which the fluid specimen is flowed and then discharged from a dispensing end of the needle portion, the means for converting the overflow fluid from said calibrated chamber into droplets is a fluid diversion valve characterized as a tubular body within which the dispensing end of the needle portion of the syringe can be positioned, the tubular body containing an outlet port through which the fluid specimen is conveyed, and a tube, one end of which is connected to said outlet port and the other end to a container into which droplets of the fluid specimen are discharged and atop which is provided said drop counting means.

5. The apparatus of claim 4 wherein the drop counting means is comprised of a bottle, a stopper assembly of tubular design which includes a lower small diameter portion which projects into and seals a neck of the bottle and an upper large diameter portion, a cap mating with and covering said large diameter portion of said stopper assembly sufficiently elongate to provide an inner chamber, an open-centered washer type support located within said chamber, the open center being coaxially aligned with the tubular opening through said stopper assembly, the support including a light emitter and light detector supported thereon and alternately disposed on opposite sides of the central opening of said stopper assembly across which a beam of light is projected and detected to count the falling drops of the fluid specimen.

6. In apparatus characterized as a fluid injector useful for the measurement and injection of preselected quantities of a fluid specimen into a medium such as an inlet to an analytical instrument which includes the combination of (A) a syringe assembly inclusive of a barrel into which a fluid specimen can be loaded, a needle mounted on an end of the barrel through the bore of which fluid specimen from the barrel can be flowed and overflowed via a dispensing end of the needle, a fluid diversion valve characterized as a tubular body within which the dispensing end of the needle can be positioned for receipt of fluid overflowed from the dispensing end of the needle, an outlet port through which the fluid specimen can be passed, and a tube, one end of which is connected to said outlet port and the other end to a container into which droplets of the fluid specimen are discharged, and means for the displacement of the fluid specimen from said barrel via the dispensing end of the needle into said inlet to the analytical instrument, (B) an injector feed assembly comprised of a probe sub-assembly inclusive of a pair of hollow needles which provide conduit means for the pick up of said fluid specimen and transport of said fluid specimen to the barrel of said syringe, and (C) a magazine for transporting one or more fluid specimen-containing septum sealed vials for pick up by said pair of hollow needles of said probe sub-assembly for delivery to the barrel of said syringe via thrust of the probe through the septum of a vial, pressurizing the contents of the vial by delivery of gas from a source through a first of said hollow needles of said probe sub-assembly to produce flow of fluid specimen from the vial into the second of the pair of hollow needles for transport through the probe sub-assembly to the barrel of the syringe, the improvement wherein the combination further includes (D) drop counting means communicated with said tube leading from the outlet port of said fluid diversion valve through which fluid specimen overflowing the syringe via the dispensing end of the needle is flowed to the container, for monitoring and counting a preselected number of the drops of the fluid specimen, and means responsive to said drop counting means for interrupting the flow of fluid specimen transported from a vial via the probe sub-assembly to trap said fluid specimen within the barrel of the syringe prior to injection of a measured quantity of the fluid specimen into the inlet of said analytical instrument.

7. The apparatus of claim 6 wherein the barrel of the syringe is provided with a valve through which fluid specimen from the second hollow needle of the probe sub-assembly is introduced, the container portion of the drop counting means is a bottle upon an upper neck portion of which is supported a stopper assembly comprised of a tubular plug, a lower projecting portion which is sealed within the neck of the bottle, and an upper portion which projects outside the neck of the bottle.

an open centered cap, the lower open side of which fits upon, mates with and is sealed upon the upper portion of said tubular plug, said cap being sufficiently elongate to provide a chamber between an upwardly faced top of the plug and lower inside surface of said cap, tubular connecting means operatively associated with the central opening in the cap and opening through said tubular plug, to which the tube is communicated for the transport of drops of fluid specimen to said drop counting means, an element of washer-like shape, round and open centered, fitted and supported on the upper face of said plug within the chamber formed between said upper face of said plug and the lower inside face of said cap, a light emitter supported on an upper face of said element, a detector supported on the upper face of said element alternately disposed on the opposite side of the opening of said element and oriented to receive a continuous beam of light emitted from said light emitter, electrical means for counting a preselected number of the falling drops which pass through and interrupt the beam of light, and means for closure of said fluid diversion valve to cut off the flow of fluid specimen to the barrel of the syringe when said preselected number of drops have been counted.

8. The apparatus of claim 7 wherein the tubular connecting means between the tube which conveys droplets of fluid specimen from the dispensing end of the needle and the drop counting means is comprised of a light transparent tubular member which extends through the central cap opening and tubular opening of the plug, and said tube is sealed upon the upper end thereof.

9. The apparatus of claim 7 wherein the projecting lower end of the plug is of relatively small diameter, and the upper end of the plug is of relatively large diameter.

10. The apparatus of claim 9 wherein both the lower and upper ends of the plug are provided with O-rings to provide an air tight fit between the lower projection end of the plug and neck of the bottle, and between the upper end of the plug and cap, respectively.

* * * * *